United States Patent [19]

Lake et al.

[11] Patent Number: 5,525,593
[45] Date of Patent: Jun. 11, 1996

[54] MEDICINAL USE OF IFG-II

[75] Inventors: Mats Lake, Lidingö ; Eva Jennische, Göteborg, both of Sweden

[73] Assignee: Pharmacia AB, Stockholm, Sweden

[21] Appl. No.: 162,019

[22] PCT Filed: Jun. 11, 1992

[86] PCT No.: PCT/SE92/00397

§ 371 Date: Dec. 3, 1993

§ 102(e) Date: Jan. 26, 1994

[87] PCT Pub. No.: WO92/22311

PCT Pub. Date: Dec. 23, 1992

[30] Foreign Application Priority Data

Jun. 14, 1991 [SE] Sweden .................... 9101840

[51] Int. Cl.⁶ .................... A61K 37/02; C07K 7/10; C12N 15/00; C12P 21/02
[52] U.S. Cl. .................... 514/21; 514/2; 514/12; 514/921; 424/DIG. 13; 530/350
[58] Field of Search .................... 404/DIG. 13; 530/350; 514/2, 12, 21, 921

[56] References Cited

U.S. PATENT DOCUMENTS

| | | | |
|---|---|---|---|
| 4,783,524 | 11/1988 | Larsen et al. | 530/350 |
| 4,861,757 | 8/1989 | Antoniades et al. | 514/21 |
| 4,885,163 | 12/1989 | Shaar et al. | 514/2 |
| 4,939,135 | 7/1990 | Robertson et al. | 514/179 |
| 4,981,956 | 1/1991 | Larsen et al. | 536/27 |
| 4,983,581 | 1/1991 | Antoniades et al. | 514/12 |
| 5,019,559 | 5/1991 | Antoniades et al. | 514/12 |
| 5,035,887 | 7/1991 | Antoniades et al. | 514/21 |
| 5,057,494 | 10/1991 | Sheffield | 514/12 |
| 5,089,475 | 2/1992 | Wilmore | 514/12 |
| 5,124,316 | 6/1992 | Antoniades et al. | 514/12 |
| 5,166,191 | 11/1992 | Cronin et al. | 514/12 |
| 5,229,493 | 7/1993 | Folkman et al. | 530/350 |
| 5,256,644 | 10/1993 | Antoniades et al. | 514/12 |

FOREIGN PATENT DOCUMENTS 0216742  4/1987  European Pat. Off. .

OTHER PUBLICATIONS

Dialog Information Service, file 155, Medline, 66–91, Dialog Acc. No. 07206852, T. P. White et al., "Satellite Cell and Growth Factor Involvement in Skeletal Muscle Growth", Med Sci Sports Exerc, Oct. 1989, 21 (5 Suppl), pp. 158,163.
The Journal of Cell Biology, vol. 110, Apr. 1990, Pico Caroni et al., "Nerve Sprouting in Innervated Adult Skeletal Muscle Induced by Exposure to Elevated Levels of Insulin-Like Growth Factors", pp. 1307–1317.
17th Annual Meeting of the Society for Neuroscience—Insulinlike Growth Factor–II Gene Expression in Muscle: "Relationship to Synapse Elimination and Nerve Regeneration", D. N. Ishii, New Orleans, Louisiana, USA, Nov. 16–21, 1987, Soc. Neurosci. Abstr. 13(2), 1987.
Acta Physiol Scand, vol. 130, 1987, E. Jennische et al., "Regenerating Skeletal Muscle Cells Express Insulin–Like Growth Factor I", pp. 327–332.
Chemical Abstracts, vol. 108, No. 21, May 23, 1988, (Columbus, Ohio, US), Robert S. Bar et al., "IGF–Receptors in Myocardial Capillary Endothelium: Potential Regulation of IGF–I Transport to Cardiac Muscle", p. 163, Abstract 180989j, & Biochem. Biophys. Res. Commun. 1988, 152(1), 93–98.

*Primary Examiner*—Ronald W. Griffin
*Attorney, Agent, or Firm*—Burns, Doane, Swecker & Mathis

[57] ABSTRACT

The use of IGF-II for preparing a medicament for the regeneration of muscle tissue; and methods for medical treatment for the purpose of regenerating muscle tissue, for minimizing scar formation during healing of a wound or for preventing undesired tissue adhesion after injury, such as after surgery.

10 Claims, 6 Drawing Sheets

MEDICINAL USE OF IFG-II

In connection with extensive research in experimentation it has now surprisingly been found that IGF-II effectively promotes regeneration of muscle tissue, whereas IGF-I does not. Thus, experiments in vivo on rate show that IGF-II significantly promotes regeneration of muscle tissue thus making the peptide useful in the treatment of muscle tissue. A similar experiment concerning wound healing in cardiac muscle unexpectedly showed increased healing and/or decreased scar formation. This is a new finding since it is established knowledge that cardiac tissue does not regenerate.

Accordingly, it is the main object of the present invention to provide new techniques for preparing medicaments effective in improving the regeneration of muscle tissue.

Another object of the invention is to provide for a medicament useful in the healing of cardiac muscle tissue.

A third object of the invention is to provide techniques for preparing a medicament for use in the healing of smooth muscle tissue, such as intestinal smooth muscle tissue.

Still another object is to provide a method for medical treatment for the purpose of regenerating muscle tissue.

Accordingly, the invention resides in the use of IGF-II for preparing a medicament for the regeneration of muscle tissue. According to a preferred aspect of the invention such use is directed to the preparation of a medicament for use in the healing of cardiac muscle tissue. An alternative aspect of the invention resides in the use of IGF-II for preparing a medicament for use in the healing of intestinal smooth muscle tissue.

The invention also resides in a method for medical treatment resulting in improved regeneration of muscle tissue. Said method includes the step of administering to a patient in need of corresponding treatment an effective amount of IGF-II.

The medicinal composition used in accord with the present invention may thus in accordance with traditional pharmaceutical practice be formulated for use in human or veterinary medicine for therapeutic purposes. Such compositions may include the active ingredient IGF-II in combination with a pharmaceutically acceptable carrier, which may be solid, semisolid or liquid.

The compositions include those in a form adapted for topical application but may also be designed for administration through other routes.

Suitable forms of the composition used in applying the techniques of the present invention include tablets, capsules, syrups, suspensions, solutions and forms suitable for injection or infusion. The latter forms intended for injection or infusion are preferred. Such compositions may contain conventional pharmaceutically acceptable materials, such as diluents, binders, colors, flavors, preservatives, disintegrates and the like in accordance with conventional pharmaceutical practice in a manner well understood by those skilled in the art of formulating drugs.

Injectable or infusable compositions of IGF-II are particularly suitable as levels of IGF-II can occur after administration by injection or infusion at the site of muscle tissue subject to regenerative healing. A particularly preferred site for cardiac treatment is the pericardium, and the administration can take different forms, such as infusion or implantation of a slow release formulation containing IGF-II.

The administered does of the active ingredient, IGF-II, may vary between broad limits, but a preferred range may be between about 0.1 and about 10 mg per day for a week. The dose is, of course, dependent on the degree and type of damage, type and condition of the patient and will be determined from case to case.

The present invention will be further illustrated in the following by specific examples which are not to be construed as limiting the scope of the invention otherwise than the definition in the appended claims. This illustration of the invention will be made with reference to the appended drawings, wherein:

FIGS. 5a–d illustrate sections through rat cardiac muscles comparing controls with IGF-II treated samples.

EXAMPLE 1

Administration of IGF-I and IGF-II on Skeletal Muscle

In this example the animals used were male Sprague-Dawley rats, body weight about 225 g. The animals were anesthetized and the substances tested and the vehicle for control, 0.1% (v/v), bovine serum albumin in physiological saline, were infused directly into extensor digitorum longus of the rate via a thin, PE10, catheter inserted into the muscle and connected to a minipump. The total dose given was 0.2 ml administered during one week. The total dose during said week was 30 μg of IGF-I and IGF-II, respectively.

After concluded administration the treated muscles were made subject to a fixing operation. Samples from the infused area were taken, on the one hand for plastic embedment for light and electron microscopy, on the other hand for sections of frozen materials for immunohistochemistry.

RESULTS

Figure 1A:
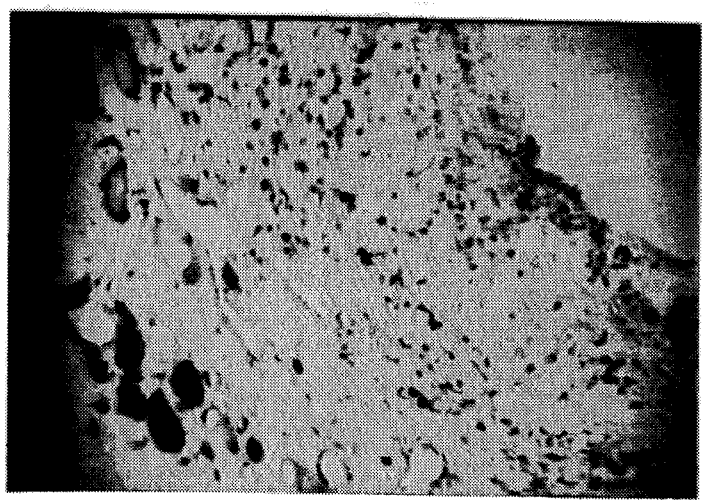
FIGS. 1a, 1b and 1c illustrate sections through frozen tissue samples, FIG. 1a being control sample, FIG. 1b sample after treatment with IGF-I and FIG. 1c sample after treatment with IGF-II.
Figure 1B:
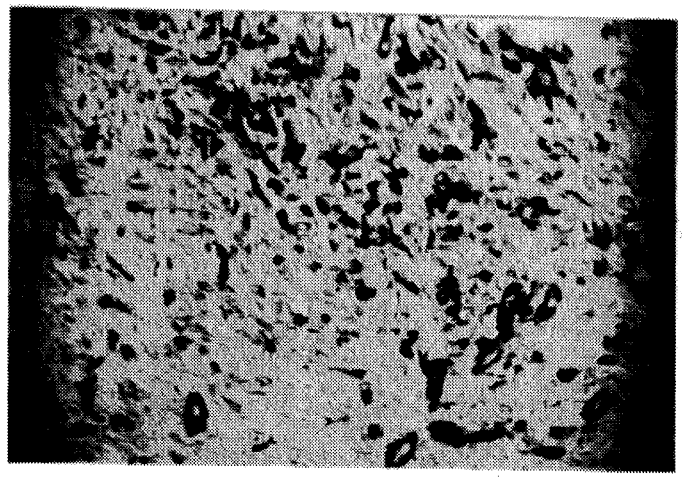
Figure 1C:
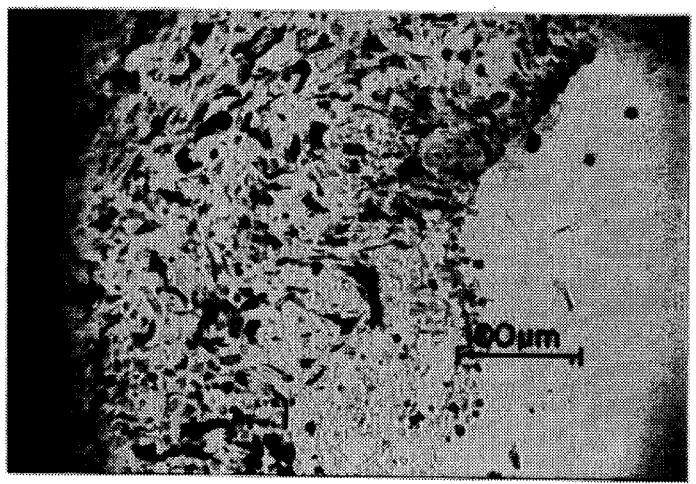
Figure 2A:
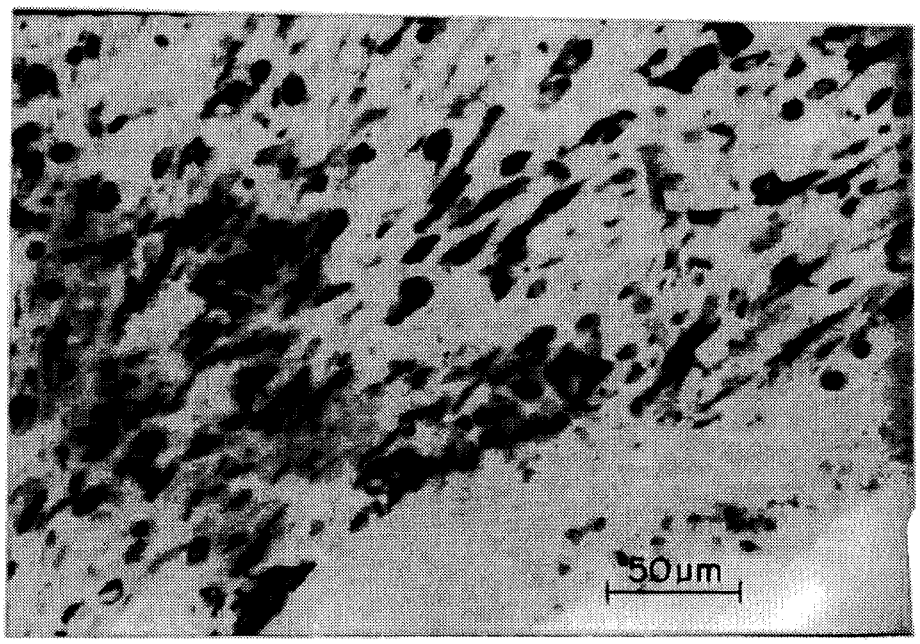
FIG. 2a is an enlarged detail of the section of FIG. 1c.
Figure 2B:
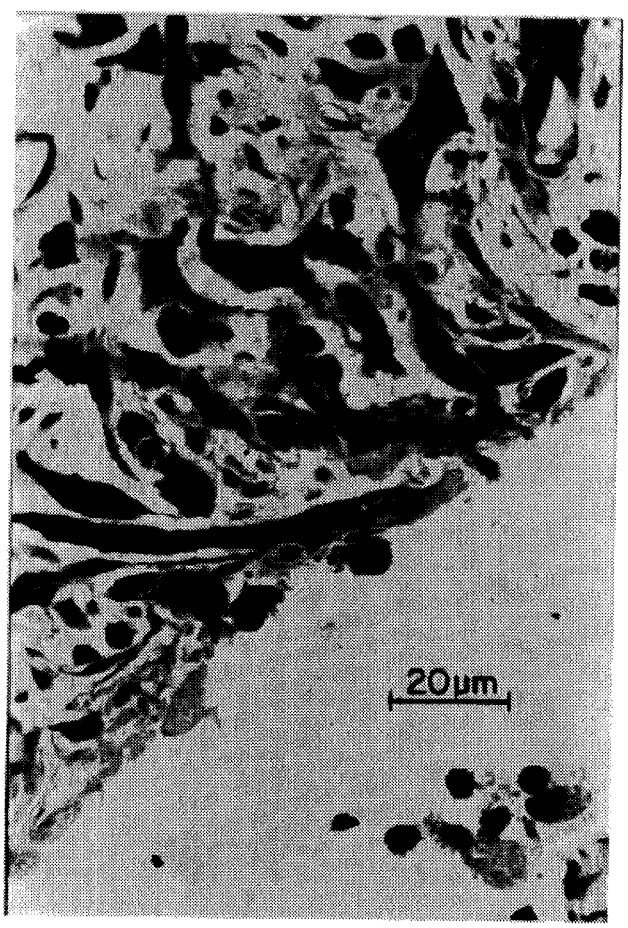
FIG. 2b is a section through a plastic embedded sample also corresponding to FIG. 1c.

FIGS. 1a, 1b and 1c illustrate sections through frozen tissue, FIG. 1a being a control using only vehicle but no IGF, and FIGS. 2b and 2c showing corresponding sections of samples after treatment with IGF-I and IGF-II, respectively.

In animals infused with only vehicle "normal" granulation tissue is formed around the catheter, said tissue containing fibroblasts, blood vessels and some inflammatory cells (FIG. 1a). In animals infused with IGF-I in the same vehicle approximately the same picture is found indicating no significant effect generated by IGF-I (FIG. 1b).

Figure 3A:
FIGS. 3a and 3b illustrate cross-sections through plastic-embedded samples, FIG. 3a illustrating the result of light microscopy and FIG. 3b showing the result of electron microscopy.
Figure 3B:
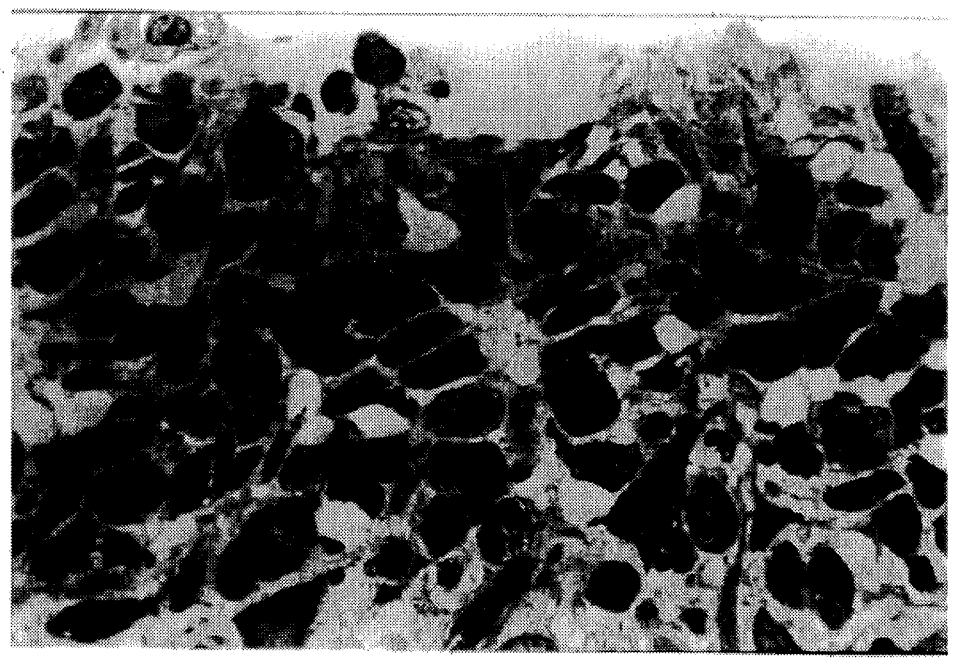

On the other hand, in animals infused with IGF-II in the same vehicle rather small elongate cells, often polynuclear, are found (FIG. 3b, plastic embedded section). The corresponding cells in cryo-section were desmin-positive, i.e. muscle cells (FIGS. 1c and 2a).

In interpreting the results it is seen that cells originating from IGF-II treatment are more differentiated than cells from IGF-I treatment.

EXAMPLE 2

Example 1 was repeated for comparison between IGF-II and IGF-I, a total dose of both of 30 μg being administered during one week. FIGS. 3a and 3b illustrate sections of plastic embedded tissue after treatment with IGF-II, and FIGS. 4a and 4b show corresponding sections after treatment with IGF-I.

It is seen from the results obtained that IGF-II acts differently and more efficiently than dose IGF-I. It is seen that IGF-II results in a relatively homogeneous population of desmin-positive cells adjacent to the catheter, and said cells have a tendency to arrange themselves in bundles relatively closely arranged. A few such groups have been indicated in FIGS. 3a and 3b. There are relatively few blood vessels in the area adjacent to the catheter which indicates that IGF-II has no effect on the angiogenesis.

Figure 4A:
FIGS. 4a and 4b illustrate corresponding sections through tissue samples treated with IGF-I.
Figure 4B:

In comparison IGF-I results in some proliferation of desmin-positive cells, but said cells are more scattered and do not tend to arrange in bundles in the same manner as after treatment with IGF-II (FIGS. 4a and 4b). It is also seen that whereas IGF-II initiates selective proliferation of desmin-positive cells, IGF-I, in addition to weak proliferation of such cells, activates also other cell components, as fibroblasts and blood vessels. This observation is a clear indication that IGF-II, contrary to IGF-I, is useful in the regeneration of muscle tissue at a site of damage. Thus, it can be seen that the treatment with IGF-II results in a well differentiated and structured muscle tissue thus eliminating the scar tissue that normally is irreversibly formed.

Model for Local Treatment of Heart Muscle Injury in Rats

Male Sprague-Dawley rats, weighing about 350 g are used. They are allowed free access to food and water throughout the experiments.

Muscle Injury

Muscle injury is induced by intramuscular injection of Marcain. Marcain injection results in a selective damage to muscle cells, while the blood vessels are spared (Butcher 1989). The animals are anaesthetized with penthobarbital, 45 mg/kg b.w. intraperitoneally. An abdominal midline incision is made and, by penetrating the diaphragm, 0.25 ml of Marcain (2.5 mg/ml) is injected into the apical part of the myocardium.

The midline incision is then closed and the animals are allowed to recover.

Treatment of the Injury

Drugs to be investigated are infused into the pericardium through a catheter connected to an osmotic pump (alzet, model 2ML 1, pumping 7 days; or model 2ML 2, pumping 14 days). The catheter is inserted into the pericardium by a modified Seldinger technique.

At a preselected time after induction of the heart muscle injury the animals are again anaesthetized with penthobarbital, 45 mg/kg b.w., and the midline incision is re-opened.

A Venflon catheter (1.7 mm OD) is inserted a short distance into the pericardium, through the diaphragm, making sure not to damage the heart wall with the needle. The steel needle is then withdrawn, leaving the plastic catheter in place. A silastic tubing (0.025 in. ID; 0.047 in. OD) is inserted through the catheter into the pericardium and finally, the Venflon catheter is withdrawn leaving the silastic tubing in the pericardial sac. The silastic tubing is secured to the abdominal wall by 6/0 silk sutures and is then connected to the osmotic pump in the peritoneum. After suturing the incision the animals are allowed to recover.

At the end of the experiment, after one or two weeks depending on the pump used, the animals are anesthetized. The correct position of the silastic tubing is controlled by injecting a small volume of methylene blue through it. The animals are fixed by transcardial perfusion with 4% buffered formaldehyde, taking care not to interfere with the area injured by the Marcain injection. After post-fixation for a further 3 hours the hearts are transferred to phosphate-buffered saline containing 7.5% sucrose, and are kept at +4° C. until further processing.

Histology

The progression of the healing process is assessed by immunostainings for intermediate filaments and acting isoforms and by light microscopy on plastic sections.

The apical part of each heart is divided by a sagittal section through the injured area. One part is embedded into methacrylate plastic (Historesin, Reichart-Jung) and cut into 1 µm thick sections. From the other part serial cryostat sections are prepared and stained with monoclonal antibodies against desmin (Dakopat), vimentin (Dakopat). The immunoreaction is visualized by a secondary HRP-linked antibody (Amersham) followed by the DAB reaction.

EXAMPLE 3

Following the procedure outlined above 5 µg of IGF-II per day are administered for 7 days. This IGF-II treatment is initiated 3 days after injection of Marcain. 0.1% BSA is used as a control. Treatment with BSA normally results in the formation of scar tissue with connected tissue and proliferating fibroblasts and granulation vessels.

Figure 5A:
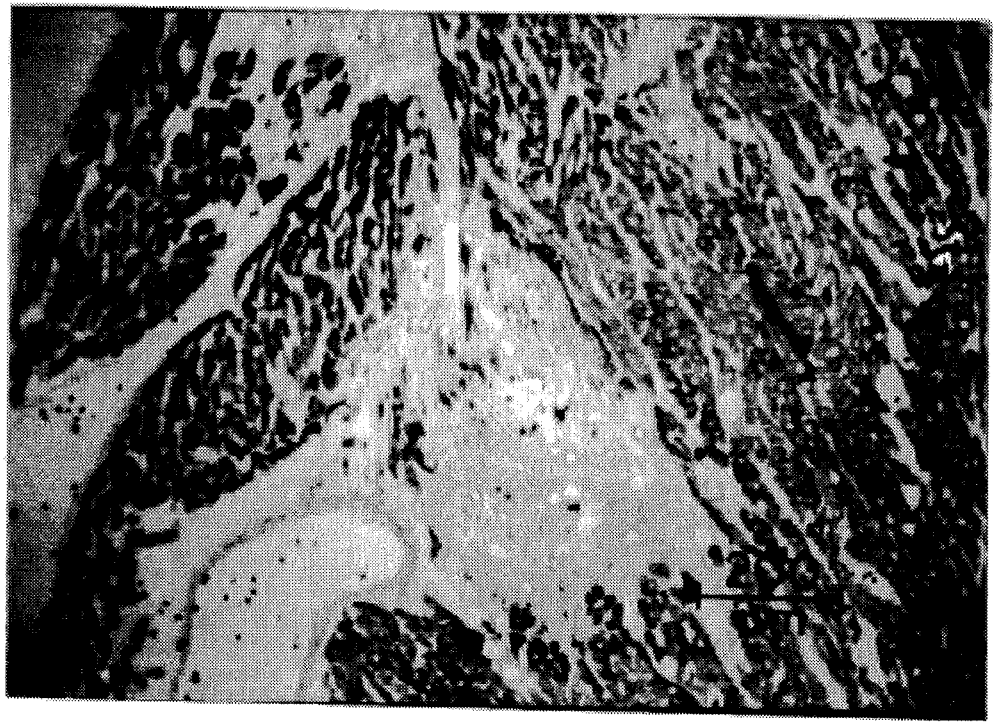
Figure 5B:
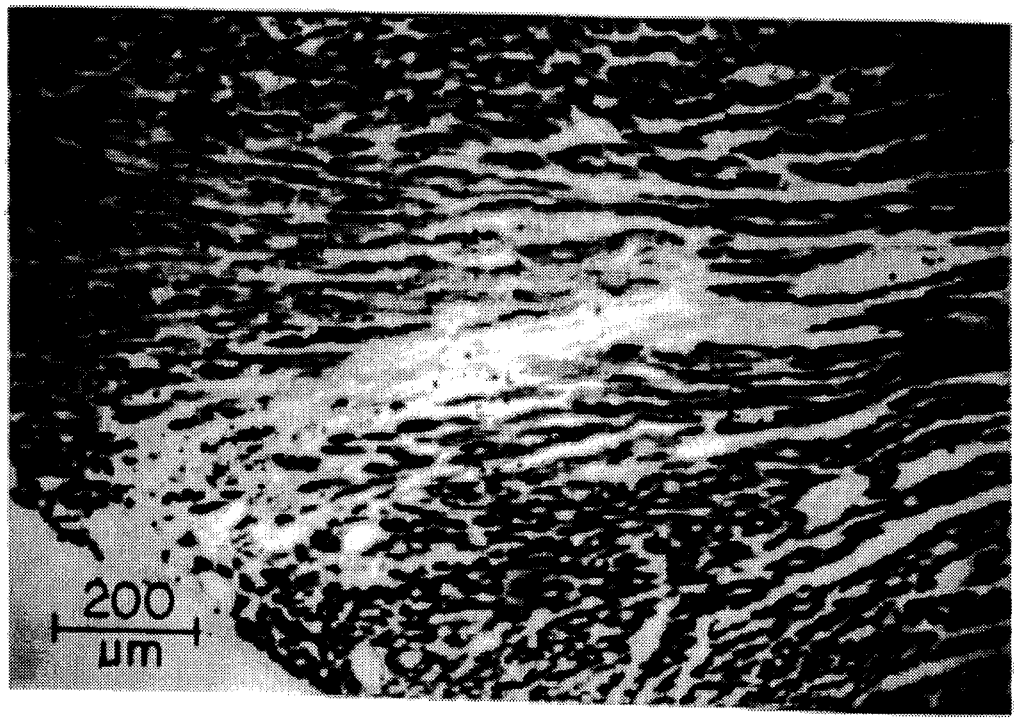

The result of the IGF-II treatment is illustrated in FIG. 5a–d. FIG. 5a and 5b illustrate control and IGF-II treatment, respectively, using staining with monoclonal antibodies against desmin. The white area enclosing the arrow indicates the damaged area in the cardiac muscle section, and it can be seen from comparison between said area of 5a and of 5b that a significant regeneration and healing has taken place due to the IGF-II treatment.

Figure 5C:
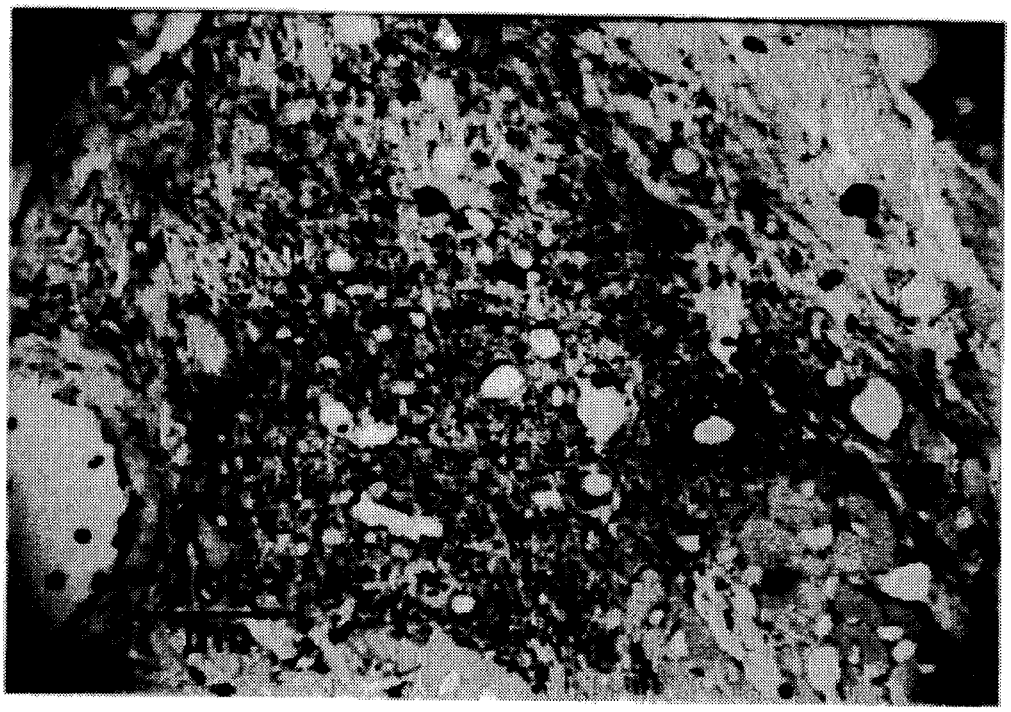
Figure 5D:
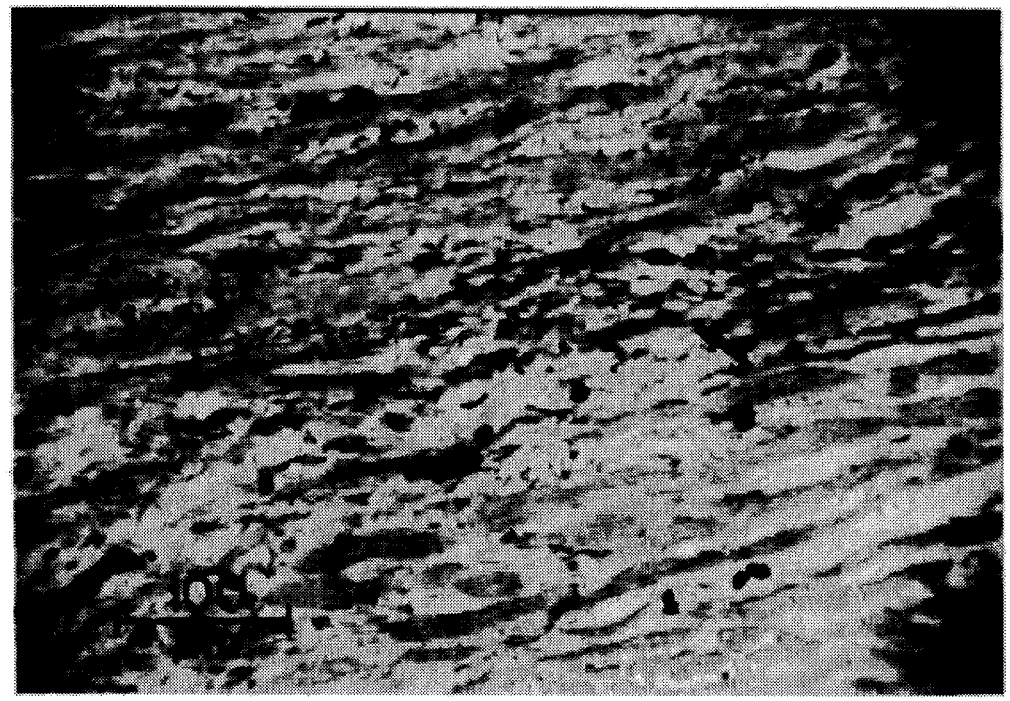

FIG. 5c and 5d show a corresponding comparison between control and IGF-II treated sample using vimentin for the staining, and comparison between 5a and 5b reflects an essential improvement in the healing process by the IGF-II treatment.

EXAMPLE 4

Example 3 is repeated but the IGF-II dose is doubled to 10 µg per day. The result of the IGF-II treatment is reflected by an astonishing enlargement of the rat cardiac muscle compared to the control. Histological investigation does not indicate any connective tissue proliferation or damages which can be observed in secondary hypertrophy in connection with hypertonia. This unexpected result is a clear indication of usefulness of IGF-II treatment for the recovery of cardiac muscle capacity upon cardiac infarct.

One particular indication where the present invention will be very useful is in the restoration of the performance on heart failure, i.e. coronary infarct. Many, if not all, of coronary infarct patients have to bear with an impaired coronary function in view of the formation of scar tissue in the cardiac muscle. Such scar tissue lacks the contracting/pumping function of normal cardiac muscle tissue and will thus result in reduced cardiac capacity.

The present invention will also be useful in the treatment of other smooth muscle tissue, such as vessel walls and intestinal walls, where healing and tissue regeneration will be positively affected.

We claim:

1. A method for the minimization of scar formation during the healing of a wound cardiac muscle tissue or smooth muscle tissue, said method comprising administering an effective amount of IGF-II to minimize scar formation to a wounded patient in need in healing cardiac muscle tissue or smooth muscle tissue.

2. A method for the minimization of scar formation during the healing of a wound according to claim 1, wherein undesired tissue adhesion during said healing is minimized.

3. A method for the minimization of scar formation during the healing of a wound according to claim 2, wherein said wound was created by surgery.

4. A method according to claim 1 wherein a pharmaceutically acceptable carrier additionally is present during said administration of said IGF-II.

5. A method according to claim 2 wherein a pharmaceutically acceptable carrier additionally is present during said administration of and IGF-II.

6. A method according to claim 3 wherein a pharmaceutically acceptable carrier additionally is present during said administration of and IGF-II.

7. A method for the regeneration of cardiac muscle tissue or smooth muscle tissue, said method comprising administering an effective amount of IGF-II to regenerate cardiac muscle tissue or smooth muscle tissue to a patient in need of such regeneration.

8. A method for the regeneration of cardiac muscle tissue or smooth muscle tissue according to claim 7 wherein said IGF-II is administered topically at the site of defective cardiac muscle tissue.

9. A method according to claim 7 wherein a pharmaceutically acceptable carrier additionally is present during said administration of said IGF-II.

10. A method according to claim 8 wherein a pharmaceutically acceptable carrier additionally is present during said administration of said IGF-II.

* * * * *